(12) United States Patent
Venugopala et al.

(10) Patent No.: US 11,912,683 B1
(45) Date of Patent: Feb. 27, 2024

(54) (6-METHYL-4-SUBSTITUTEDPHENYL-2-OXO/THIOXO-1,2,3,4-TETRAHYDROPYRIMIDIN-5-YL)(PIPERIDIN-1-YL)METHANONES AS ANTITUBERCULAR AGENTS

(71) Applicant: KING FAISAL UNIVERSITY, Al-Ahsa (SA)

(72) Inventors: Katharigatta N. Venugopala, Al-Ahsa (SA); Keshab M. Bairagi, Maharashtra (IN); Pran Kishore Deb, Mesra (IN); Melendran Pillay, Durban (ZA); Mohamed A. Morsy, Al-Ahsa (SA); Susanta K. Nayak, Maharashtra (IN); Sandeep Chandrashekharappa, Raebareli (IN); Osama I. Alwassil, Riyadh (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/367,645

(22) Filed: Sep. 13, 2023

(51) Int. Cl.
*C07D 401/06* (2006.01)
*A61P 31/06* (2006.01)
*C07D 403/06* (2006.01)

(52) U.S. Cl.
CPC .......... *C07D 401/06* (2013.01); *A61P 31/06* (2018.01); *C07D 403/06* (2013.01)

(58) Field of Classification Search
CPC .......................... C07D 401/06; C07D 403/06
See application file for complete search history.

(56) References Cited

FOREIGN PATENT DOCUMENTS

| BR | 102018068863 A2 | 3/2020 |
|---|---|---|
| WO | 2007105233 A2 | 9/2007 |
| WO | 2016004028 A1 | 1/2016 |

OTHER PUBLICATIONS

Chen et al. Letters in Organic Chemistry, 2014, 11, 643-650.*
Yadlapalli et al. Tetrahedron Letters 53 (2012) 6725-6728.*
Yadlapalli, et al., "A Facile One-Pot Synthesis of 2-Thioxo-Dihydropyrimidines and Polyfunctionalized Pyran Derivatives as Mimics of Novel Calcium Channel Modulators", Tetrahedron Letters, vol. 53, Issue 49, Dec. 5, 2012, pp. 6725-6728.

* cited by examiner

*Primary Examiner* — Rebecca L Anderson
(74) *Attorney, Agent, or Firm* — Nath, Goldberg & Meyer; Richard C. Litman

(57) ABSTRACT

Compounds for treating tuberculosis and, particularly, anti-tubercular compounds that are (6-methyl-4-substitutedphenyl-2-oxo/thioxo-1,2,3,4-tetrahydropyrimidin-5-yl)(piperidin-1-yl)methanones and their use as anti-tubercular agents are provided.

3 Claims, No Drawings

(6-METHYL-4-SUBSTITUTEDPHENYL-2-OXO/THIOXO-1,2,3,4-TETRAHYDROPYRIMIDIN-5-YL)(PIPERIDIN-1-YL)METHANONES AS ANTITUBERCULAR AGENTS

BACKGROUND

1. Field

The present disclosure relates to compounds for treating tuberculosis and, particularly, to anti-tubercular compounds that are (6-methyl-4-substituted phenyl-2-oxo/thioxo-1,2,3,4-tetrahydropyrimidin-5-yl)(piperidin-1-yl)methanone derivatives and their use as antitubercular agents, including as antitubercular agents against MDR strains of *Mycobacterium tuberculosis*.

2. Description of the Related Art

Tuberculosis (TB) is a communicable infectious disease and a major cause of illness, particularly in low-income countries. It is caused by the opportunistic *bacillus Mycobacterium tuberculosis* (MTB), which primarily attacks the lungs (pulmonary), but may later affect other parts (extra-pulmonary) of the body. Several factors have contributed to the continuous health threat of TB globally, including the development of drug resistance, such as multidrug-resistant tuberculosis (MDR-TB), extensively drug-resistant tuberculosis (XDR-TB), and totally drug-resistant tuberculosis (TDR-TB); the co-morbidities with acquired immunodeficiency syndrome (AIDS), and the risks involved in developing diabetes mellitus among TB patients. New therapeutic strategies are needed to combat the tuberculosis pandemic and the growing resistance to conventional anti-TB drugs, which remain a serious public health challenge worldwide.

In the past forty years, very few new anti-tubercular (anti-TB) drugs have been approved, with the exception of Bedaquiline (Approved in 2012 by the US-FDA), Delamanid (Approved in 2014 in Europe), and Pretomanid (Approved in 2019 by the US-FDA). As these drugs are typically not effective by themselves, they are usually combined with first-line and second-line anti-TB drugs. These conventional anti-TB drugs are associated with significant side effects. Further, clinical resistance to conventional anti-TB drugs has been widely reported in extensively drug-resistant tuberculosis (XDR-TB) patients.

Tetrahydropyrimidine represents a privileged scaffold for the development of bioactive compounds. Several synthetic tetrahydropyrimidines have been reported to possess a broad spectrum of pharmacological activities, such as polymorphism and larvicidal (Bairagi K. M., Venugopala K. N., Mondal P. K., Gleiser R. M., Chopra D, Garcia D, et al. Larvicidal study of tetrahydropyrimidine scaffolds against *Anopheles arabiensis* and structural insight by single crystal x-ray studies. Chem Biol Drug Des. 2018; 92:1924-1932, Venugopala K. N., Nayak S. K., Gleiser R. M., Sanchez-Borzone M. E., Garcia D. A., Odhav B. Synthesis, polymorphism, and insecticidal activity of methyl 4-(4-chlorophenyl)-8-iodo-2-methyl-6-oxo-1, 6-dihydro-4H-pyrimido [2, 1-b] quinazoline-3-carboxylate against *Anopheles arabiensis* mosquito. Chem Biol Drug Des. 2016; 88:88-96), anti-tubercular (Venugopala K. N., Nayak S. K., Pillay M, Prasanna R, Coovadia Y. M., Odhav B. Synthesis and antitubercular activity of 2-(substituted phenyl/benzyl-amino)-6-(4-chlorophenyl)-5-(methoxycarbonyl)-4-methyl-3, 6-dihydropyrimidin-1-ium chlorides. Chem Biol Drug Des. 2013; 81:219-227), thymidylate kinase inhibitors (Venugopala K. N., Tratrat C, Pillay M, Chandrashekharappa S, Al-Attraqchi O. H. A., Aldhubiab B. E., et al. In silico design and synthesis of tetrahydropyrimidinones and tetrahydropyrimidinethiones as potential thymidylate kinase inhibitors exerting anti-TB activity against *Mycobacterium tuberculosis*. Drug Des Devel Ther. 2020; 14:1027), anti-mosquito (Venugopala K. N., Gleiser R. M., Chalannavar R. K., Odhav B. Antimosquito properties of 2-substituted phenyl/benzylamino-6-(4-chlorophenyl)-5-methoxycarbonyl-4-methyl-3, 6-dihydropyrimidin-1-ium chlorides against *Anopheles arabiensis*. Med Chem. 2014; 10:211-219), antidiabetic (Bairagi K. M., Younis N. S., Emeka P. M., Sangtani E, Gonnade R. G., Venugopala K. N., et al. Antidiabetic activity of dihydropyrimidine scaffolds and structural insight by single crystal x-ray studies. Med Chem. 2020; 16:996-1003, Bairagi K. M., Younis N. S., Emeka P. M., Venugopala K. N., Alwassil O. I., Khalil H. E., et al. Chemistry, anti-diabetic activity and structural analysis of substituted dihydropyrimidine analogues. J Mol Struct. 2021; 1227:129412), anthelmintic (Chitikina S. S., Buddiga P, Deb P. K., Mailavaram R. P., Venugopala K. N., Nair A. B., et al. Synthesis and anthelmintic activity of some novel (E)-2-methyl/propyl-4-(2-(substitutedbenzylidene) hydrazinyl)-5, 6, 7, 8-tetrahydrobenzo[4, 5] thieno[2, 3-d] pyrimidines. Med Chem Res. 2020; 29:1600-1610) and polymorphism property (Panini P, Venugopala K. N., Odhav B, Chopra D. Polymorphism in two biologically active dihydropyrimidinium hydrochloride derivatives: Quantitative inputs towards the energetics associated with crystal packing. Acta Crystal Section B. 2014; 70:681-696). Thus, anti-tubercular compounds solving the aforementioned problems are desired.

SUMMARY

In the process of discovering a novel anti-tubercular (anti-TB agent) with a new molecular mechanism of action, a series of (6-methyl-4-substitutedphenyl-2-oxo/thioxo-1,2,3,4-tetrahydropyrimidin-5-yl)(piperidin-1-yl)methanone s has been developed by a synthetic chemical method and purified by a column chromatographic method. Structural elucidation of the compounds has been completed by spectral techniques such as FT-IR, and NMR ($^1$H and $^{13}$C). These compounds have been found to possess anti-TB activity against H37Rv and, multi-drug resistance (MDR) strains of *Mycobacterium tuberculosis*. Some compounds show promising anti-tubercular activity at millimolar to micromolar concentrations when tested alone against whole-cell *Mycobacterium tuberculosis* organisms.

In an embodiment, the present subject matter relates to a compound having the formula I:

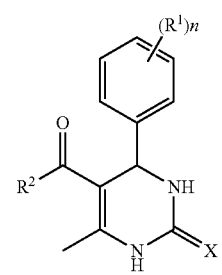

or a pharmaceutically acceptable salt, ester, stereoisomer, or solvate thereof, wherein:

R₁ is selected from the group consisting of hydrogen, fluorine, trifluoromethyl, —NO₂, bromine, methoxy, methyl, chlorine, and hydroxy;

R₂ is selected from the group consisting of piperidine, methoxy, and pyrrolidine;

X is O or S; and n is 1 or 2.

In another embodiment, the present subject matter relates to a method of treating tuberculosis in a patient, comprising administering to a patient in need thereof a therapeutically effective amount of a compound having the formula I:

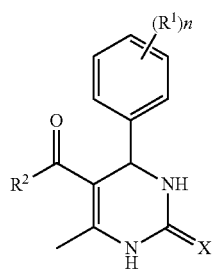

or a pharmaceutically acceptable salt, ester, stereoisomer, or solvate thereof, wherein:

R₁ is selected from the group consisting of hydrogen, fluorine, trifluoromethyl, —NO₂, bromine, methoxy, methyl, chlorine, and hydroxy;

R₂ is selected from the group consisting of piperidine, methoxy, and pyrrolidine;

X is O or S; and n is 1 or 2.

In a further embodiment, the present subject matter relates to a compound having the formula I:

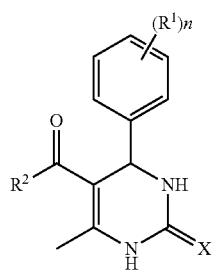

or a pharmaceutically acceptable salt, ester, stereoisomer, or solvate thereof, wherein:

R₁ is selected from the group consisting of methyl, hydroxy, hydrogen, and trifluoromethyl;

R₂ is selected from the group consisting of piperidine and pyrrolidine;

X is S; and n is 1 or 2.

In another embodiment, the present subject matter relates to a method of treating tuberculosis in a patient, comprising administering to a patient in need thereof a therapeutically effective amount of a compound having the formula I:

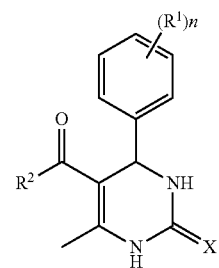

or a pharmaceutically acceptable salt, ester, stereoisomer, or solvate thereof, wherein:

R₁ is selected from the group consisting of methyl, hydroxy, hydrogen, and trifluoromethyl;

R₂ is selected from the group consisting of piperidine and pyrrolidine;

X is S; and n is 1 or 2.

In a further embodiment, the present subject matter relates to a compound selected from the group consisting of: (6-Methyl-4-phenyl-2-thioxo-1,2,3,4-tetrahydropyrimidin-5-yl)(piperidin-1-yl)methanone (DHPM-KN1); (4-(4-Fluorophenyl)-6-methyl-2-thioxo-1,2,3,4-tetrahydropyrimidin-5-yl)(piperidin-1-yl)methanone (DHPM-KN2); Methyl 6-methyl-2-thioxo-4-(4-(trifluoromethyl)phenyl)-1,2,3,4-tetrahydropyrimidine-5-carboxylate (DHPM-KN3); Methyl 4-(2,4-dinitrophenyl)-6-methyl-2-oxo-1,2,3,4-tetrahydropyrimidine-5-carboxylate (DHPM-KN4); (6-Methyl-4-(4-nitrophenyl)-2-thioxo-1,2,3,4-tetrahydropyrimidin-5-yl)(piperidin-1-yl)methanone (DHPM-KN5); (4-(4-Bromophenyl)-6-methyl-2-thioxo-1,2,3,4-tetrahydropyrimidin-5-yl)(piperidin-1-yl)methanone (DHPM-KN6); (4-(4-Methoxyphenyl)-6-methyl-2-thioxo-1,2,3,4-tetrahydropyrimidin-5-yl)(piperidin-1-yl)methanone (DHPM-KN7); (6-Methyl-2-thioxo-4-(o-tolyl)-1,2,3,4-tetrahydropyrimidin-5-yl)(piperidin-1-yl)methanone (DHPM-KN8); (4-(4-Chlorophenyl)-6-methyl-2-thioxo-1,2,3,4-tetrahydropyrimidin-5-yl)(piperidin-1-yl)methanone (DHPM-KN9); (6-Methyl-2-thioxo-4-(4-(trifluoromethyl)phenyl)-1,2,3,4-tetrahydropyrimidin-5-yl)(piperidin-1-yl)methanone (DHPM-KN10); (4-(4-Hydroxyphenyl)-6-methyl-2-thioxo-1,2,3,4-tetrahydropyrimidin-5-yl)(piperidin-1-yl)methanone (DHPM-KN11); (4-(2-Hydroxyphenyl)-6-methyl-2-thioxo-1,2,3,4-tetrahydropyrimidin-5-yl)(piperidin-1-yl)methanone (DHPM-KN12); (4-(3,4-Dihydroxyphenyl)-6-methyl-2-thioxo-1,2,3,4-tetrahydropyrimidin-5-yl)(piperidin-1-yl)methanone (DHPM-KN13); (6-Methyl-4-phenyl-2-thioxo-1,2,3,4-tetrahydropyrimidin-5-yl)(pyrrolidin-1-yl)methanone (DHPM-KN14); and a pharmaceutically acceptable salt, ester, stereoisomer, or solvate thereof.

In a further embodiment, the present subject matter relates to a compound selected from the group consisting of: (6-Methyl-2-thioxo-4-(o-tolyl)-1,2,3,4-tetrahydropyrimidin-5-yl)(piperidin-1-yl)methanone (DHPM-KN8); (6-Methyl-2-thioxo-4-(4-(trifluoromethyl)phenyl)-1,2,3,4-tetrahydropyrimidin-5-yl)(piperidin-1-yl)methanone (DHPM-KN10); (4-(2-Hydroxyphenyl)-6-methyl-2-thioxo-1,2,3,4-tetrahydropyrimidin-5-yl)(piperidin-1-yl)methanone (DHPM-KN12); (4-(3,4-Dihydroxyphenyl)-6-methyl-2-thioxo-1,2,3,4-tetrahydropyrimidin-5-yl)(piperidin-1-yl)methanone (DHPM-KN13); (6-Methyl-4-phenyl-2-thioxo-1,2,3,4-tetrahydropyrimidin-5-yl)(pyrrolidin-1-yl)

methanone (DHPM-KN14); and a pharmaceutically acceptable salt, ester, stereoisomer, or solvate thereof.

In yet another embodiment, the present subject matter relates to a method of treating tuberculosis in a patient, comprising administering to a patient in need thereof a therapeutically effective amount of a compound selected from the group consisting of: (6-Methyl-4-phenyl-2-thioxo-1,2,3,4-tetrahydropyrimidin-5-yl)(piperidin-1-yl)methanone (DHPM-KN1); (4-(4-Fluorophenyl)-6-methyl-2-thioxo-1,2,3,4-tetrahydropyrimidin-5-yl)(piperidin-1-yl)methanone (DHPM-KN2); Methyl 6-methyl-2-thioxo-4-(4-(trifluoromethyl)phenyl)-1,2,3,4-tetrahydropyrimidine-5-carboxylate (DHPM-KN3); Methyl 4-(2,4-dinitrophenyl)-6-methyl-2-oxo-1,2,3,4-tetrahydropyrimidine-5-carboxylate (DHPM-KN4); (6-Methyl-4-(4-nitrophenyl)-2-thioxo-1,2,3,4-tetrahydropyrimidin-5-yl)(piperidin-1-yl)methanone (DHPM-KN5); (4-(4-Bromophenyl)-6-methyl-2-thioxo-1,2,3,4-tetrahydropyrimidin-5-yl)(piperidin-1-yl)methanone (DHPM-KN6); (4-(4-Methoxyphenyl)-6-methyl-2-thioxo-1,2,3,4-tetrahydropyrimidin-5-yl)(piperidin-1-yl)methanone (DHPM-KN7); (6-Methyl-2-thioxo-4-(o-tolyl)-1,2,3,4-tetrahydropyrimidin-5-yl)(piperidin-1-yl)methanone (DHPM-KN8); (4-(4-Chlorophenyl)-6-methyl-2-thioxo-1,2,3,4-tetrahydropyrimidin-5-yl)(piperidin-1-yl)methanone (DHPM-KN9); (6-Methyl-2-thioxo-4-(4-(trifluoromethyl)phenyl)-1,2,3,4-tetrahydropyrimidin-5-yl)(piperidin-1-yl)methanone (DHPM-KN10); (4-(4-Hydroxyphenyl)-6-methyl-2-thioxo-1,2,3,4-tetrahydropyrimidin-5-yl)(piperidin-1-yl)methano ne (DHPM-KN11); (4-(2-Hydroxyphenyl)-6-methyl-2-thioxo-1,2,3,4-tetrahydropyrimidin-5-yl)(piperidin-1-yl)methanone (DHPM-KN12); (4-(3,4-Dihydroxyphenyl)-6-methyl-2-thioxo-1,2,3,4-tetrahydropyrimidin-5-yl)(piperidin-1-yl)methanone (DHPM-KN13); (6-Methyl-4-phenyl-2-thioxo-1,2,3,4-tetrahydropyrimidin-5-yl)(pyrrolidin-1-yl)methano ne (DHPM-KN14); and a pharmaceutically acceptable salt, ester, stereoisomer, or solvate thereof.

In still yet another embodiment, the present subject matter relates to a method of treating tuberculosis in a patient, comprising administering to a patient in need thereof a therapeutically effective amount of a compound selected from the group consisting of: (6-Methyl-2-thioxo-4-(o-tolyl)-1,2,3,4-tetrahydropyrimidin-5-yl)(piperidin-1-yl)methanone (DHPM-KN8); (6-Methyl-2-thioxo-4-(4-(trifluoromethyl)phenyl)-1,2,3,4-tetrahydropyrimidin-5-yl)(piperidin-1-yl)methanone (DHPM-KN10); (4-(2-Hydroxyphenyl)-6-methyl-2-thioxo-1,2,3,4-tetrahydropyrimidin-5-yl)(piperidin-1-yl)methanone (DHPM-KN12); (4-(3,4-Dihydroxyphenyl)-6-methyl-2-thioxo-1,2,3,4-tetrahydropyrimidin-5-yl)(piperidin-1-yl)methanone (DHPM-KN13); (6-Methyl-4-phenyl-2-thioxo-1,2,3,4-tetrahydropyrimidin-5-yl)(pyrrolidin-1-yl)methanone (DHPM-KN14); and a pharmaceutically acceptable salt, ester, stereoisomer, or solvate thereof.

In another embodiment, the present subject matter relates to a method of treating tuberculosis in a patient, comprising administering to a patient in need thereof a therapeutically effective amount of a compound selected from the group consisting of: (6-Methyl-4-phenyl-2-thioxo-1,2,3,4-tetrahydropyrimidin-5-yl)(piperidin-1-yl)methanone (DHPM-KN1); Methyl 4-(2,4-dinitrophenyl)-6-methyl-2-oxo-1,2,3,4-tetrahydropyrimidine-5-carboxylate (DHPM-KN4); (6-Methyl-4-(4-nitrophenyl)-2-thioxo-1,2,3,4-tetrahydropyrimidin-5-yl)(piperidin-1-yl)methanone (DHPM-KN5); (4-(4-Bromophenyl)-6-methyl-2-thioxo-1,2,3,4-tetrahydropyrimidin-5-yl)(piperidin-1-yl)methanone (DHPM-KN6); (4-(4-Methoxyphenyl)-6-methyl-2-thioxo-1,2,3,4-tetrahydropyrimidin-5-yl)(piperidin-1-yl)methanone (DHPM-KN7); (6-Methyl-2-thioxo-4-(o-tolyl)-1,2,3,4-tetrahydropyrimidin-5-yl)(piperidin-1-yl)methanone (DHPM-KN8); (6-Methyl-2-thioxo-4-(4-(trifluoromethyl)phenyl)-1,2,3,4-tetrahydropyrimidin-5-yl)(piperidin-1-yl)methanone (DHPM-KN10); and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of treating tuberculosis by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially" of or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a compound having the formula I:

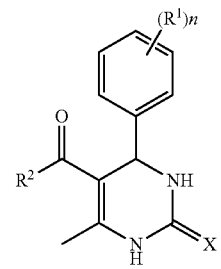

or a pharmaceutically acceptable salt, ester, stereoisomer, or solvate thereof, wherein:
  $R_1$ is selected from the group consisting of hydrogen, fluorine, trifluoromethyl, —$NO_2$, bromine, methoxy, methyl, chlorine, and hydroxy;
  $R_2$ is selected from the group consisting of piperidine, methoxy, and pyrrolidine;
  X is O or S; and
  n is 1 or 2.

In a further embodiment, the present subject matter relates to a compound having the formula I:

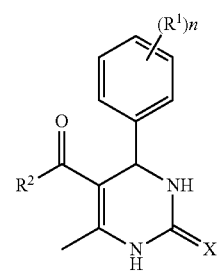

or a pharmaceutically acceptable salt, ester, stereoisomer, or solvate thereof, wherein:
  $R_1$ is selected from the group consisting of methyl, hydroxy, hydrogen, and trifluoromethyl;
  $R_2$ is selected from the group consisting of piperidine and pyrrolidine;
  X is S; and
  n is 1 or 2.

In one embodiment, $R_1$ and n, when taken together, can be selected from the group consisting of hydrogen, 4-fluorine, 4-$CF_3$, 2-$NO_2$, 4-$NO_2$, 4-bromine, 4-methoxy, 2-methyl, 4-chlorine, 4-hydroxy, 2-hydroxy, and 3,4-dihydroxy. In another embodiment, $R_1$ and n, when taken together, can be selected from the group consisting of 2-methyl, 4-$CF_3$, 2-hydroxy, 3,4-dihydroxy, and hydrogen.

In an embodiment, $R_2$ can be selected from the group consisting of piperidine and pyrrolidine. Likewise, in an embodiment, X can be S.

In yet another embodiment, the present subject matter relates to a method of treating tuberculosis in a patient, comprising administering to a patient in need thereof a therapeutically effective amount of a compound selected from the group consisting of: (6-Methyl-4-phenyl-2-thioxo-1,2,3,4-tetrahydropyrimidin-5-yl)(piperidin-1-yl)methanone (DHPM-KN1); (4-(4-Fluorophenyl)-6-methyl-2-thioxo-1,2,3,4-tetrahydropyrimidin-5-yl)(piperidin-1-yl)methanone (DHPM-KN2); Methyl 6-methyl-2-thioxo-4-(4-(trifluoromethyl)phenyl)-1,2,3,4-tetrahydropyrimidine-5-carboxylate (DHPM-KN3); Methyl 4-(2,4-dinitrophenyl)-6-methyl-2-oxo-1,2,3,4-tetrahydropyrimidine-5-carboxylate (DHPM-KN4); (6-Methyl-4-(4-nitrophenyl)-2-thioxo-1,2,3,4-tetrahydropyrimidin-5-yl)(piperidin-1-yl)methanone (DHPM-KN5); (4-(4-Bromophenyl)-6-methyl-2-thioxo-1,2,3,4-tetrahydropyrimidin-5-yl)(piperidin-1-yl)methanone (DHPM-KN6); (4-(4-Methoxyphenyl)-6-methyl-2-thioxo-1,2,3,4-tetrahydropyrimidin-5-yl)(piperidin-1-yl)methanone (DHPM-KN7); (6-Methyl-2-thioxo-4-(o-tolyl)-1,2,3,4-tetrahydropyrimidin-5-yl)(piperidin-1-yl)methanone (DHPM-KN8); (4-(4-Chlorophenyl)-6-methyl-2-thioxo-1,2,3,4-tetrahydropyrimidin-5-yl)(piperidin-1-yl)methanone (DHPM-KN9); (6-Methyl-2-thioxo-4-(4-(trifluoromethyl)phenyl)-1,2,3,4-tetrahydropyrimidin-5-yl)(piperidin-1-yl)methanone (DHPM-KN10); (4-(4-Hydroxyphenyl)-6-methyl-2-thioxo-1,2,3,4-tetrahydropyrimidin-5-yl)(piperidin-1-yl)methano ne (DHPM-KN11); (4-(2-Hydroxyphenyl)-6-methyl-2-thioxo-1,2,3,4-tetrahydropyrimidin-5-yl)(piperidin-1-yl)methanone (DHPM-KN12); (4-(3,4-Dihydroxyphenyl)-6-methyl-2-thioxo-1,2,3,4-tetrahydropyrimidin-5-yl)(piperidin-1-yl)methanone (DHPM-KN13); (6-Methyl-4-phenyl-2-thioxo-1,2,3,4-tetrahydropyrimidin-5-yl)(pyrrolidin-1-yl)methano ne (DHPM-KN14); and a pharmaceutically acceptable salt, ester, stereoisomer, or solvate thereof.

In still yet another embodiment, the present subject matter relates to a method of treating tuberculosis in a patient, comprising administering to a patient in need thereof a therapeutically effective amount of a compound selected from the group consisting of: (6-Methyl-2-thioxo-4-(o-tolyl)-1,2,3,4-tetrahydropyrimidin-5-yl)(piperidin-1-yl)methanone (DHPM-KN8); (6-Methyl-2-thioxo-4-(4-(trifluoromethyl)phenyl)-1,2,3,4-tetrahydropyrimidin-5-yl)(piperidin-1-yl)methanone (DHPM-KN10); (4-(2-Hydroxyphenyl)-6-methyl-2-thioxo-1,2,3,4-tetrahydropyrimidin-5-yl)(piperidin-1-yl)methanone (DHPM-KN12); (4-(3,4-Dihydroxyphenyl)-6-methyl-2-thioxo-1,2,3,4-tetrahydropyrimidin-5-yl)(piperidin-1-yl)methanone (DHPM-KN13); (6-Methyl-4-phenyl-2-thioxo-1,2,3,4-tetrahydropyrimidin-5-yl)(pyrrolidin-1-yl)methano ne (DHPM-KN14); and a pharmaceutically acceptable salt, ester, stereoisomer, or solvate thereof.

In another embodiment, the present subject matter relates to a method of treating tuberculosis in a patient, comprising administering to a patient in need thereof a therapeutically effective amount of a compound selected from the group consisting of: (6-Methyl-4-phenyl-2-thioxo-1,2,3,4-tetrahydropyrimidin-5-yl)(piperidin-1-yl)methanone (DHPM-KN1); Methyl 4-(2,4-dinitrophenyl)-6-methyl-2-oxo-1,2,3,4-tetrahydropyrimidine-5-carboxylate (DHPM-KN4); (6-Methyl-4-(4-nitrophenyl)-2-thioxo-1,2,3,4-tetrahydropyrimidin-5-yl)(piperidin-1-yl)methanone (DHPM-KN5); (4-(4-Bromophenyl)-6-methyl-2-thioxo-1,2,3,4-tetrahydropyrimidin-5-yl)(piperidin-1-yl)methanone (DHPM-KN6); (4-(4-Methoxyphenyl)-6-methyl-2-thioxo-1,2,3,4-tetrahydropyrimidin-5-yl)(piperidin-1-yl)methanone (DHPM-KN7); (6-Methyl-2-thioxo-4-(o-tolyl)-1,2,3,4-tetrahydropyrimidin-5-yl)(piperidin-1-yl)methanone (DHPM-KN8); (6-Methyl-2-thioxo-4-(4-(trifluoromethyl)phenyl)-1,2,3,4-tetrahydropyrimidin-5-yl)(piperidin-1-yl)methano ne (DHPM-KN10); and a pharmaceutically acceptable salt, ester, stereoisomer, or solvate thereof.

In another embodiment, the present subject matter relates to a method of treating tuberculosis in a patient, comprising administering to a patient in need thereof a therapeutically effective amount of a compound having the formula I:

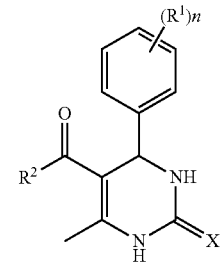

or a pharmaceutically acceptable salt, ester, stereoisomer, or solvate thereof, wherein:

$R_1$ is selected from the group consisting of hydrogen, fluorine, trifluoromethyl, —$NO_2$, bromine, methoxy, methyl, chlorine, and hydroxy;

$R_2$ is selected from the group consisting of piperidine, methoxy, and pyrrolidine;

X is O or S; and n is 1 or 2.

In one embodiment of the compounds used in the present methods, $R_1$ and n, when taken together, can be selected from the group consisting of hydrogen, 4-fluorine, 4-$CF_3$, 2-$NO_2$, 4-$NO_2$, 4-bromine, 4-methoxy, 2-methyl, 4-chlorine, 4-hydroxy, 2-hydroxy, and 3,4-dihydroxy. In another embodiment, $R_1$ and n, when taken together, can be selected from the group consisting of 2-methyl, 4-$CF_3$, 2-hydroxy, 3,4-dihydroxy, and hydrogen.

In another embodiment, the present subject matter relates to a method of treating tuberculosis in a patient, comprising administering to a patient in need thereof a therapeutically effective amount of a compound having the formula I:

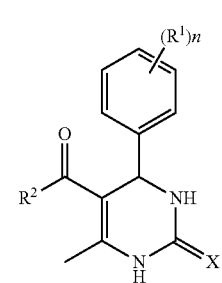

or a pharmaceutically acceptable salt, ester, stereoisomer, or solvate thereof, wherein:

$R_1$ is selected from the group consisting of methyl, hydroxy, hydrogen, and trifluoromethyl;

$R_2$ is selected from the group consisting of piperidine and pyrrolidine;

X is S; and n is 1 or 2.

In another embodiment, the present subject matter relates to a method of treating tuberculosis in a patient, comprising administering to a patient in need thereof a therapeutically effective amount of a compound having the formula I:

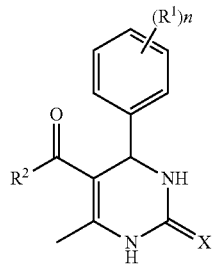

I or a pharmaceutically acceptable salt, ester, stereoisomer, or solvate thereof, wherein:
  $R_1$ is selected from the group consisting of —$NO_2$, bromine, methoxy, methyl, hydrogen, and trifluoromethyl;
  $R_2$ is selected from the group consisting of piperidine and methoxy;
  X is O or S; and
  n is 1.

In one embodiment of the compounds used in the present methods, $R_1$ and n, when taken together, can be selected from the group consisting of hydrogen, 2-$NO_2$, 4-$NO_2$, 4-bromine, 4-methoxy, 2-methyl, and 4-$CF_3$.

In yet another embodiment, the present subject matter relates to a method of treating tuberculosis in a patient, comprising administering to a patient in need thereof a therapeutically effective amount of a compound selected from the group consisting of: (6-Methyl-4-phenyl-2-thioxo-1,2,3,4-tetrahydropyrimidin-5-yl)(piperidin-1-yl)methanone (DHPM-KN1); (4-(4-Fluorophenyl)-6-methyl-2-thioxo-1,2,3,4-tetrahydropyrimidin-5-yl)(piperidin-1-yl) methanone (DHPM-KN2); Methyl 6-methyl-2-thioxo-4-(4-(trifluoromethyl)phenyl)-1,2,3,4-tetrahydropyrimidine-5-carboxylate (DHPM-KN3); Methyl 4-(2,4-dinitrophenyl)-6-methyl-2-oxo-1,2,3,4-tetrahydropyrimidine-5-carboxylate (DHPM-KN4); (6-Methyl-4-(4-nitrophenyl)-2-thioxo-1,2,3,4-tetrahydropyrimidin-5-yl)(piperidin-1-yl)methanone (DHPM-KN5); (4-(4-Bromophenyl)-6-methyl-2-thioxo-1,2,3,4-tetrahydropyrimidin-5-yl)(piperidin-1-yl)methanone (DHPM-KN6); (4-(4-Methoxyphenyl)-6-methyl-2-thioxo-1,2,3,4-tetrahydropyrimidin-5-yl)(piperidin-1-yl)methanone (DHPM-KN7); (6-Methyl-2-thioxo-4-(o-tolyl)-1,2,3,4-tetrahydropyrimidin-5-yl)(piperidin-1-yl)methanone (DHPM-KN8); (4-(4-Chlorophenyl)-6-methyl-2-thioxo-1,2,3,4-tetrahydropyrimidin-5-yl)(piperidin-1-yl)methanone (DHPM-KN9); (6-Methyl-2-thioxo-4-(4-(trifluoromethyl)phenyl)-1,2,3,4-tetrahydropyrimidin-5-yl)(piperidin-1-yl) methanone (DHPM-KN10); (4-(4-Hydroxyphenyl)-6-methyl-2-thioxo-1,2,3,4-tetrahydropyrimidin-5-yl) (piperidin-1-yl)methano ne (DHPM-KN11); (4-(2-Hydroxyphenyl)-6-methyl-2-thioxo-1,2,3,4-tetrahydropyrimidin-5-yl)(piperidin-1-yl)methanone (DHPM-KN12); (4-(3,4-Dihydroxyphenyl)-6-methyl-2-thioxo-1,2,3,4-tetrahydropyrimidin-5-yl)(piperidin-1-yl) methanone (DHPM-KN13); (6-Methyl-4-phenyl-2-thioxo-1,2,3,4-tetrahydropyrimidin-5-yl)(pyrrolidin-1-yl)methano ne (DHPM-KN14); and a pharmaceutically acceptable salt, ester, stereoisomer, or solvate thereof.

In still yet another embodiment, the present subject matter relates to a method of treating tuberculosis in a patient, comprising administering to a patient in need thereof a therapeutically effective amount of a compound selected from the group consisting of: (6-Methyl-2-thioxo-4-(o-tolyl)-1,2,3,4-tetrahydropyrimidin-5-yl)(piperidin-1-yl) methanone (DHPM-KN8); (6-Methyl-2-thioxo-4-(4-(trifluoromethyl)phenyl)-1,2,3,4-tetrahydropyrimidin-5-yl) (piperidin-1-yl)methanone (DHPM-KN10); (4-(2-Hydroxyphenyl)-6-methyl-2-thioxo-1,2,3,4-tetrahydropyrimidin-5-yl)(piperidin-1-yl)methanone (DHPM-KN12); (4-(3,4-Dihydroxyphenyl)-6-methyl-2-thioxo-1,2,3,4-tetrahydropyrimidin-5-yl)(piperidin-1-yl) methanone (DHPM-KN13); (6-Methyl-4-phenyl-2-thioxo-1,2,3,4-tetrahydropyrimidin-5-yl)(pyrrolidin-1-yl)methano ne (DHPM-KN14); and a pharmaceutically acceptable salt, ester, stereoisomer, or solvate thereof.

In another embodiment, the present subject matter relates to a method of treating tuberculosis in a patient, comprising administering to a patient in need thereof a therapeutically effective amount of a compound selected from the group consisting of: (6-Methyl-4-phenyl-2-thioxo-1,2,3,4-tetrahydropyrimidin-5-yl)(piperidin-1-yl)methanone (DHPM-KN1); Methyl 4-(2,4-dinitrophenyl)-6-methyl-2-oxo-1,2,3,4-tetrahydropyrimidine-5-carboxylate (DHPM-KN4); (6-Methyl-4-(4-nitrophenyl)-2-thioxo-1,2,3,4-tetrahydropyrimidin-5-yl)(piperidin-1-yl)methanone (DHPM-KN5); (4-(4-Bromophenyl)-6-methyl-2-thioxo-1,2,3,4-tetrahydropyrimidin-5-yl)(piperidin-1-yl)methanone (DHPM-KN6); (4-(4-Methoxyphenyl)-6-methyl-2-thioxo-1,2,3,4-tetrahydropyrimidin-5-yl)(piperidin-1-yl)methanone (DHPM-KN7); (6-Methyl-2-thioxo-4-(o-tolyl)-1,2,3,4-tetrahydropyrimidin-5-yl)(piperidin-1-yl)methanone (DHPM-KN8); (6-Methyl-2-thioxo-4-(4-(trifluoromethyl)phenyl)-1,2,3,4-tetrahydropyrimidin-5-yl)(piperidin-1-yl)methanone (DHPM-KN10); and a pharmaceutically acceptable salt, ester, stereoisomer, or solvate thereof.

Said differently, the present subject matter can relate to compounds of formula I and to methods of treating tuberculosis using compounds of formula I, i.e., (6-Methyl-4-substitutedphenyl-2-oxo/thioxo-1,2,3,4-tetrahydropyrimidin-5-yl)(piperidin-1-yl)methanones, or pharmaceutically acceptable salts, esters, stereoisomers, or solvates thereof, having the following formulae:

DHPM-KN1

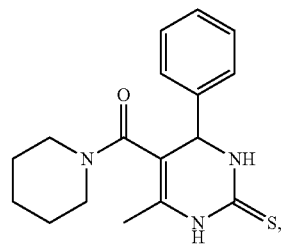

DHPM-KN2

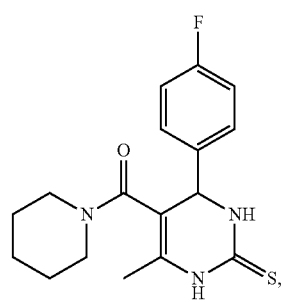

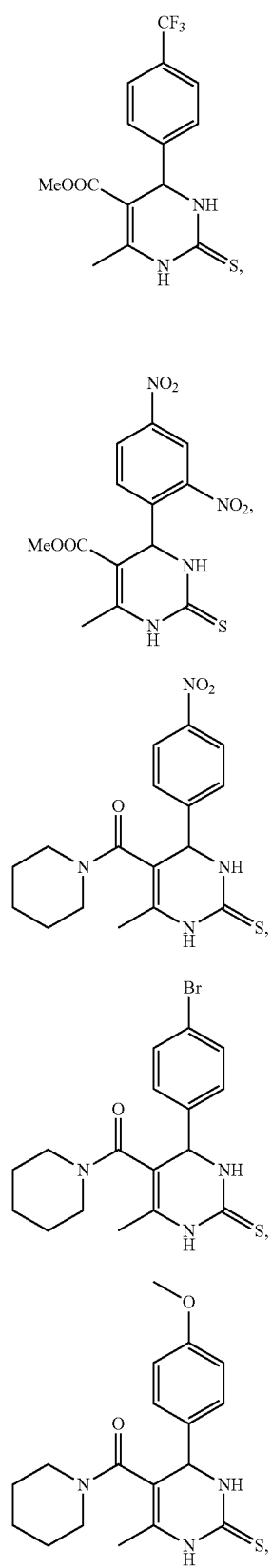
DHPM-KN3
DHPM-KN4
DHPM-KN5
DHPM-KN6
DHPM-KN7
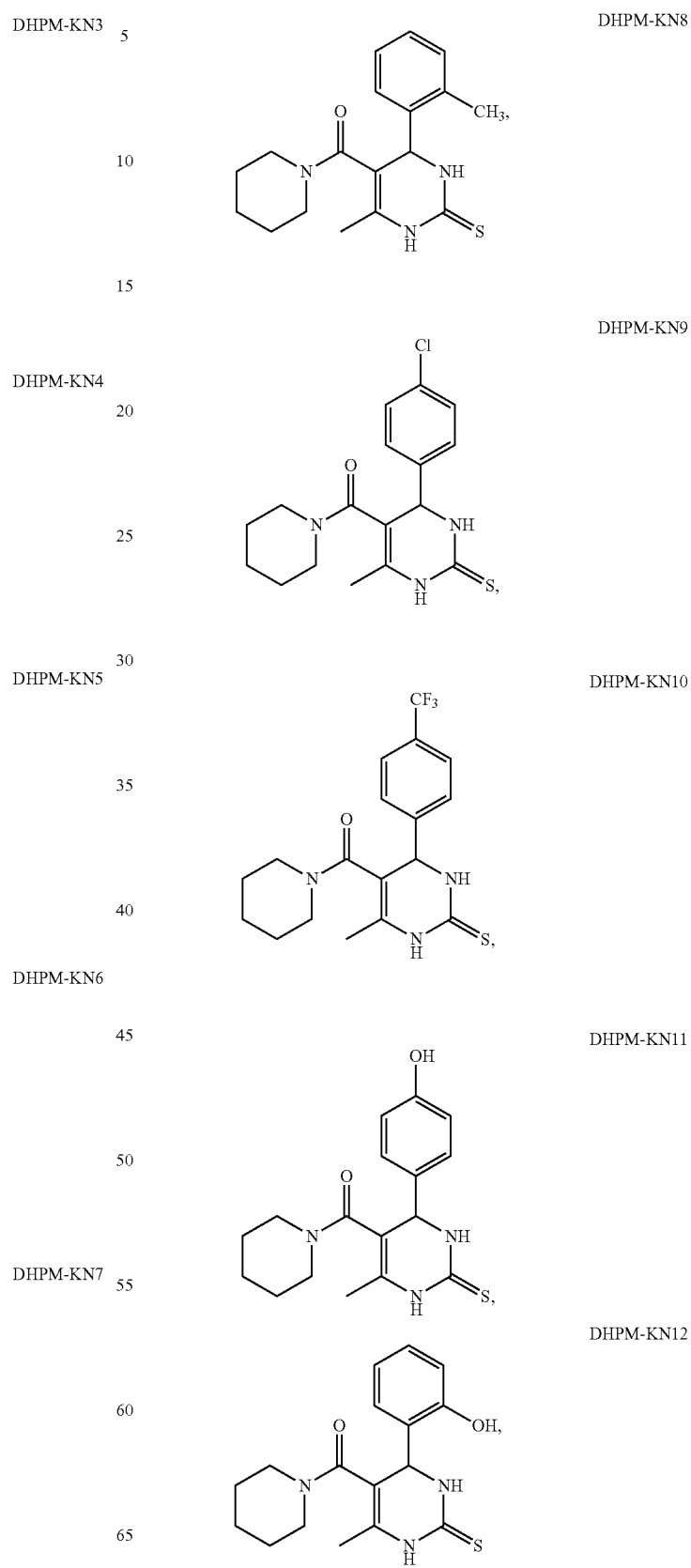
DHPM-KN8
DHPM-KN9
DHPM-KN10
DHPM-KN11
DHPM-KN12

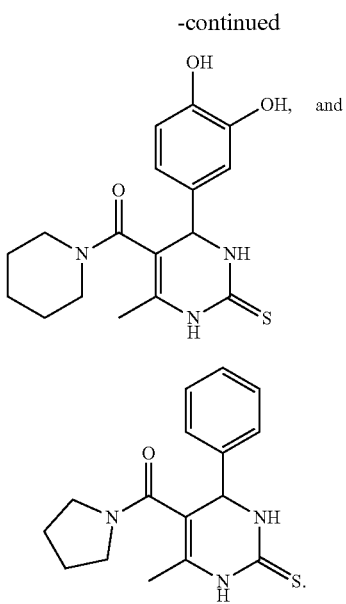

DHPM-KN13

DHPM-KN14

It is to be understood that the present subject matter covers all combinations of substituent groups referred to herein.

The present compounds may contain, e.g., when isolated in crystalline form, varying amounts of solvents. Accordingly, the present subject matter includes methods of using all solvates of the present compounds of formula I and pharmaceutically acceptable stereoisomers, esters, and/or salts thereof. Hydrates are one example of such solvates.

Further, the present subject matter includes methods of using all mixtures of possible stereoisomers of the embodied compounds, independent of the ratio, including the racemates.

Salts of the compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

The present compounds can exhibit anti-TB activity against H37Rv and multiple drug resistant (MDR) strains of *Mycobacterium tuberculosis*. The compounds can exhibit anti-TB properties at millimolar to micromolar concentrations against whole cell *Mycobacterium tuberculosis* organisms. Accordingly, the anti-tubercular compounds can be effective agents for treating tuberculosis.

In one embodiment, the compounds used in the present methods can be prepared according to the following general synthetic pathway as shown in Scheme 1.

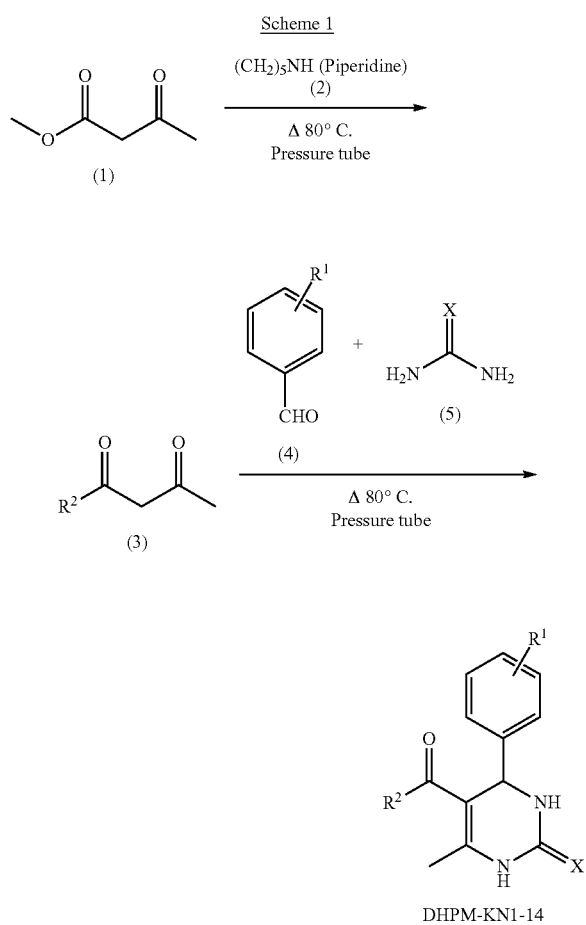

DHPM-KN1: $R^1$ = H; $R^2$ = -(CH$_2$)$_5$N; X = S DHPM-KN2: $R^1$ = 4-F; $R^2$ = -(CH$_2$)$_5$N; X = S DHPM-KN3: $R^1$ = 4-CF$_3$; $R^2$ = -OMe; X = S DHPM-KN4: $R^1$ = 2-NO$_2$, 4-NO$_2$; $R^2$ = -OMe; X = O DHPM-KN5: $R^1$ = 4-NO$_2$; $R^2$ = -(CH$_2$)$_5$N; X = S DHPM-KN6: $R^1$ = 4-Br; $R^2$ = -(CH$_2$)$_5$N; X = S DHPM-KN7: $R^1$ = 4-OCH$_3$; $R^2$ = -(CH$_2$)$_5$N; X = S DHPM-KN8: $R^1$ = 2-CH$_3$; $R^2$ = -(CH$_2$)$_5$N; X = S DHPM-KN9: $R^1$ = 4-Cl; $R^2$ = -(CH$_2$)$_5$N; X = S DHPM-KN10: $R^1$ = 4-CF$_3$; $R^2$ = -(CH$_2$)$_5$N; X = S DHPM-KN11: $R^1$ = 4-OH; $R^2$ = -(CH$_2$)$_5$N; X = S DHPM-KN12: $R^1$ = 2-OH; $R^2$ = -(CH$_2$)$_5$N; X = S DHPM-KN13: $R^1$ = 3-OH, 4-OH; $R^2$ = -(CH$_2$)$_5$N; X = S DHPM-KN14: $R^1$ = H; $R^2$ = -(CH$_2$)$_4$N; X = S

In this regard, a synthetic scheme for the present compounds can include a one-pot synthesis by taking a combination of an equimolar mixture of ethyl acetoacetate 1 and piperidine 2 in a pressure tube and stirring at about 75° C. to about 80° C. for at least about 18 hrs. The completion of the reaction is monitored by TLC. The same reaction mixture, benzaldehyde or substituted benzaldehyde 4 and thiourea 5 are added and continuously stirred at about 75° C. to about 80° C. for at least about 24 hrs. The completion of the reaction is monitored by TLC. The crude reaction mixture is purified. The obtained compounds are further dried/evaporated under a vacuum oven. The yield of compounds obtained is more than 50%, as per Scheme 1, above. The details of synthesized compounds are tabulated in Table 1.

TABLE 1

The synthesized compounds details of (6-methyl-4-substitutedphenyl-2-thioxo-1,2,3,4-tetrahydropyrimidin-5-yl)(piperidin-1-yl) methanones (DHPM-KN1-14) using pressure tube.

| Compound code | $R^1$ | $R^2$ | X | M.P (° C.) | Yield % | cLogP* |
|---|---|---|---|---|---|---|
| DHPM-KN1 | H | -(CH$_2$)$_5$N | S | 240 | 82 | 3.2456 |
| DHPM-KN2 | 4-F | -(CH$_2$)$_5$N | S | 234 | 79 | 3.3886 |
| DHPM-KN3 | 4-CF$_3$ | -Ome | S | 190 | 86 | 4.1086 |
| DHPM-KN4 | 2-NO$_2$, 4-NO$_2$ | -Ome | O | 210 | 90 | 1.5018 |
| DHPM-KN5 | 4-NO$_2$ | -(CH$_2$)$_5$N | S | 230 | 84 | 2.9886 |
| DHPM-KN6 | 4-Br | -(CH$_2$)$_5$N | S | 258 | 87 | 3.1084 |
| DHPM-KN7 | 4-OCH$_3$ | -(CH$_2$)$_5$N | S | 124 | 88 | 3.1646 |
| DHPM-KN8 | 4-CH$_3$ | -(CH$_2$)$_5$N | S | 260 | 78 | 3.7446 |
| DHPM-KN9 | 4-Cl | -(CH$_2$)$_5$N | S | 218 | 81 | 3.9486 |
| DHPM-KN10 | 4-CF$_3$ | -(CH$_2$)$_5$N | S | 172 | 83 | 4.1286 |
| DHPM-KN11 | 4-OH | -(CH$_2$)$_5$N | S | 274 | 86 | 2.5786 |
| DHPM-KN12 | 2-OH | -(CH$_2$)$_5$N | S | 223 | 85 | 2.5286 |
| DHPM-KN13 | 3-OH,4-OH | -(CH$_2$)$_5$N | S | 173 | 87 | 1.9816 |
| DHPM-KN14 | H | -(CH$_2$)$_4$N | S | 198 | 74 | 2.6866 |

*The partition coefficient value cLogP was calculated using Chem Bio Draw Ultra 13.0v.

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for tuberculosis. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of tuberculosis, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of diseases such as tuberculosis.

An embodiment of the present subject matter is directed to a method of treating tuberculosis in a patient, comprising administering to a patient in need thereof a therapeutically effective amount of a compound as described herein or a pharmaceutically acceptable composition as described herein. A therapeutically effective amount of the compound or pharmaceutically acceptable composition or an amount effective to treat a disease, such as tuberculosis, may be determined initially from the Examples described herein and adjusted for specific targeted diseases using routine methods.

In an embodiment, the tuberculosis can comprise multiple drug resistant (MDR) strains of *Mycobacterium tuberculosis*. In another embodiment, the tuberculosis can comprise H37Rv strains of *Mycobacterium tuberculosis*. In certain embodiments, one or more different forms, strains, or types of tuberculosis may be treated independently or simultaneously.

Accordingly, in an embodiment of the present subject matter, the present compounds as described herein engaged for in vitro study towards H37Rv and multidrug-resistant (MDR) strains of *Mycobacterium tuberculosis*, can display an MIC with a nano to micromolar concentration range. For example, a present compound engaged for in vitro study against susceptible (H37Rv) strains of *Mycobacterium tuberculosis* can display an MIC concentration of about 128, about 64, about 16, or about 8 µg/mL. For the avoidance of doubt, the present compounds can display an MIC concentration in the range of any two endpoints as described herein.

In another example, a present compound engaged for in vitro study against multidrug-resistant (MDR) strains of *Mycobacterium tuberculosis* can display an MIC concentration of about 256, about 128, about 64, or about 32 µg/mL. For the avoidance of doubt, the present compounds can display an MIC concentration in the range of any two endpoints as described herein.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The present subject matter can be better understood by referring to the following examples.

EXAMPLES

Example 1

Solvent and catalyst-free synthesis of (6-methyl-4-substitutedphenyl-2-thioxo-1,2,3,4-tetrahydropyrimidin-5-yl)(piperidin-1-yl)methanones (DHPM-KN1-14) using pressure tube Compounds DHPM-KN1-DHPM-KN14 were synthesized according to the following Scheme 1.

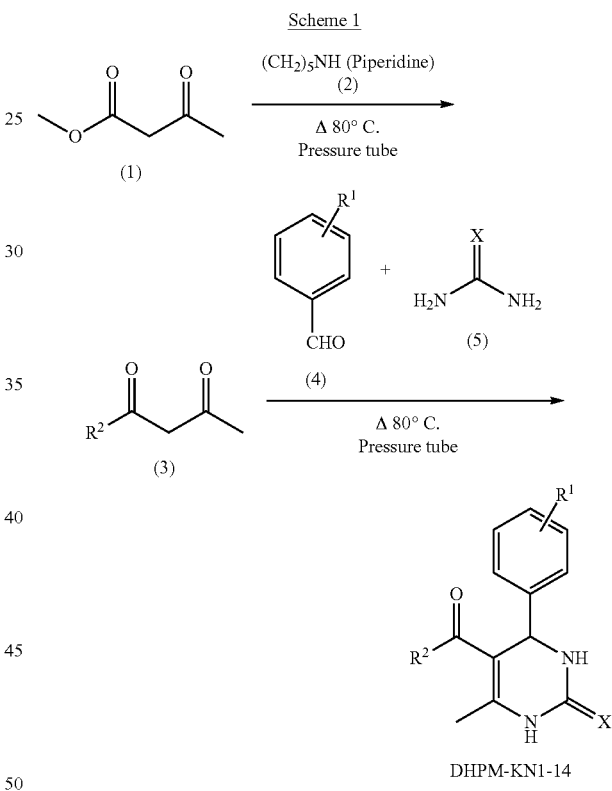

DHPM-KN1-14

DHPM-KN1: R¹ = H; R² = -(CH₂)₅N; X = S DHPM-KN2: R¹ = 4-F; R² = -(CH₂)₅N; X = S DHPM-KN3: R¹ = 4-CF₃; R² = -OMe; X = S DHPM-KN4: R¹ = 2-NO₂, 4-NO₂; R² = -OMe; X = O DHPM-KN5: R¹ = 4-NO₂; R² = -(CH₂)₅N; X = S DHPM-KN6: R¹ = 4-Br; R² = -(CH₂)₅N; X = S DHPM-KN7: R¹ = 4-OCH₃; R² = -(CH₂)₅N; X = S DHPM-KN8: R¹ = 2-CH₃; R² = -(CH₂)₅N; X = S DHPM-KN9: R¹ = 4-Cl; R² = -(CH₂)₅N; X = S DHPM-KN10: R¹ = 4-CF₃; R² = -(CH₂)₅N; X = S DHPM-KN11: R¹ = 4-OH; R² = -(CH₂)₅N; X = S DHPM-KN12: R¹ = 2-OH; R² = -(CH₂)₅N; X = S DHPM-KN13: R¹ = 3-OH, 4-OH; R² = -(CH₂)₅N; X = S DHPM-KN14: R¹ = H; R² = -(CH₂)₄N; X = S

General synthetic procedure for the synthesis of (6-methyl-4-substitutedphenyl-2-thioxo-1,2,3,4-tetrahydropyrimidin-5-yl)(piperidin-1-yl)methanones (DHPM-KN1-14)

A combination of an equimolar mixture of ethyl acetoacetate 1 (1.52 g, 11.74 mmol) and piperidine 2 (1 g, 11.74 mmol) was taken in a 60 mL pressure tube and stirred at 80° C. for 18 hrs. The completion of the reaction was monitored by TLC. The same reaction mixture, benzaldehyde or substituted benzaldehyde 4 (1.19 g, 11.2 mmol) and thiourea 5 (0.855 g, 11.2 mmol) were added and continuously stirred at 80° C. for 24 hrs. The completion of the reaction was monitored by TLC. The crude reaction mixture was purified by column chromatography by using 60-120 mesh silica gel with pet ether and ethyl acetate as an eluent. The obtained compounds were further dried/evaporated under a vacuum oven. The yield of compounds obtained was more than 50% (Scheme 1). The physicochemical properties of the title compounds are tabulated in Table 1, above.

The characterization details for the compounds (DHPM-KN1-14) are reported below.

(6-Methyl-4-phenyl-2-thioxo-1,2,3,4-tetrahydropyrimidin-5-yl) (piperidin-1-yl) methanone (DHPM-KN1)

Appearance: Brown solid; IR (KBR) v/cm 3440, 3210, 3026, 2879, 2702, 1700, 1685, 1445, 1232, 835; 1 H NMR (400 MHz, DMSO-d6) δ=9.79 (—N—H, s, 1H), 9.06 (—N—H, s, 1H), 7.29-7.08 ($C_6H_3$, 5H), 4.96 (—CH, 1H), 2.92 (—$CH_2$, m, 4H), 2.43 (—$CH_2$, s, 6H), 1.60 (—$CH_3$, s, 3H). $^{13}$C NMR (100 MHz, DMSO-d6) δ=173.69, 165.08, 142.81, 128.17, 127.90, 127.64, 126.08, 125.32, 105.89, 56.78, 43.60 24.99, 23.56, 20.70, 15.17.

(4-(4-Fluorophenyl)-6-methyl-2-thioxo-1,2,3, 4-tetrahydropyrimidin-5-yl) (piperidin-1-yl) methanone (DHPM-KN2)

Appearance: pale yellow solid; IR (KBR) v/cm 3340, 3110, 3050, 2870, 2708, 1705, 1680, 1441, 1230, 750; 1 H NMR (400 MHz, DMSO-d6) δ=9.81 (—N—H, s, 1H), 9.06 (—N—H, s, 1H), 7.1 ($C_6H_3$, 4H), 4.96 (—CH, 1H), 2.92 (—$CH_2$, m, 2H), 2.41 (—$CH_2$, s, 6H), 1.60 (—$CH_3$, s, 3H), 1.30 (—$CH_2$, s, 2H). $^{13}$C NMR (100 MHz, DMSO-d6) δ=174.46, 166.48, 163.55, 161.12, 127.90, 139.88, 129.11, 128.74, 126.16, 116.23, 116.01, 106.55, 56.85, 44.44, 25.97, 24.42, 22.87, 21.45, 16.03.

Methyl 6-methyl-2-thioxo-4-(4-(trifluoromethyl)phenyl)-1,2,3,4-tetrahydropyrimidine-5-carboxylate (DHPM-KN3)

Appearance: Brown solid; IR (KBR) v/cm 3440, 3210, 3100, 3050, 2890, 2700, 1685, 1515, 1190, 650; 1 H NMR (400 MHz, DMSO-d6) δ=10.10 (—N—H, s, 1H), 9.38 (—N—H, s, 1H), 7.37 ($C_6H_2$, 2H), 7.10 ($C_6H_2$, 2H), 4.96 (—CH, 1H), 3.20 (—$CH_3$, m, 3H), 1.95 (—$CH_3$, s, 3H); $^{13}$C NMR (100 MHz, DMSO-d6) δ=174.67, 156.80, 147.81, 146.19, 0.128.50, 127.51, 125.97, 125.74, 100.12, 53.86, 51.50, 17.51.

Methyl 4-(2,4-dinitrophenyl)-6-methyl-2-oxo-1,2,3, 4-tetrahydropyrimidine-5-carboxylate (DHPM-KN4)

Appearance: Pale yellow solid; IR (KBR) v/cm 3382, 2935, 1689, 1641, 1480, 1270, 1180, 1085, 730; 1 H NMR (400 MHz, DMSO-d6) δ=9.49 (—N—H, s, 1H), 8.55 (—N—H, s, 1H), 8.42-7.77 ($C_6H_3$, 3H), 5.76 (—CH, 1H), 3.29 (—$CH_3$, m, 3H), 2.17 (—$CH_3$, s, 3H), $^{13}$C NMR (100 MHz, DMSO-d6) δ=165.29, 151.29, 150.73, 147.48, 146.85, 145.77, 131.36, 128.66, 119.78, 97.58, 51.23, 49.78, 18.23.

(6-Methyl-4-(4-nitrophenyl)-2-thioxo-1,2,3,4-tetrahydropyrimidin-5-yl)(piperidin-1-yl)methanone (DHPM-KN5)

Appearance: white; IR (KBR) v/cm 3375, 2923, 1680, 1649, 1489, 1260, 1170, 1030, 835, 730; 1 H NMR (400 MHz, DMSO-d6) δ=9.62 (—N—H, s, 1H), 8.85 (—N—H, s, 1H), 7.83 ($C_6H_2$, 2H), 7.02 ($C_6H_2$, 2H), 4.77 (—CH, 1H), 2.58 (—$CH_2$, s, 3H), 2.08 (—$CH_2$, s, 6H), 1.29 (—$CH_3$, s, 3H); $^{13}$C NMR (100 MHz, DMSO-d6) δ=174.20, 165.51, 149.88, 147.03, 137.78, 128.14, 127.75, 125.52, 124.06, 104.85, 62.06, 25.51, 23.76, 20.82, 15.51.

(4-(4-Bromophenyl)-6-methyl-2-thioxo-1,2,3,4-tetrahydropyrimidin-5-yl)(piperidin-1-yl)methanone (DHPM-KN6)

Appearance: yellow; IR (KBR) v/cm 3475, 3152, 2920, 1706, 1549, 1389, 1269, 1189, 1031, 850; 1 H NMR (400 MHz, DMSO-d6) δ=9.96 (—N—H, s, 1H), 9.17 (—N—H, s, 2H), 7.57-7.13 ($C_6H_4$, 4H), 5.45 (—CH, 1H), 3.75 (—$CH_2$, m, 4H), 1.66 (—$CH_3$, s, 3H), 1.04 (—$CH_2$, s, 6H); $^{13}$C NMR (100 MHz, DMSO-d6) δ=174.21, 165.03, 137.77, 129.87, 128.67, 128.13, 125.52, 120.62, 62.05, 25.51, 23.79, 20.82, 15.17.

(4-(4-Methoxyphenyl)-6-methyl-2-thioxo-1,2,3,4-tetrahydropyrimidin-5-yl)(piperidin-1-yl)methanone (DHPM-KN7)

Appearance: brown; IR (KBR) v/cm 3360, 3162, 2930, 1699, 1500, 1300, 1268, 1180, 1058, 760; 1 H NMR (400 MHz, DMSO-d6) δ=9.43 (—N—H, s, 1H), 8.69 (—N—H, s, 2H), 7.09-6.54 ($C_6H_4$, 4H), 4.58 (—CH, 1H), 3.44 (—$CH_2$, m, 4H), 2.66 (—$CH_3$, s, 3H), 1.90 (—$CH_3$, s, 3H), 1.29 (—$CH_2$, s, 4H), 0.64 (—$CH_2$, s, 2H); $^{13}$C NMR (100 MHz, DMSO-d6) δ=173.67, 166.02, 158.98, 137.88, 127.67, 125.53, 114.04, 106.41, 79.22, 62.07, 55.26, 25.52, 20.83, 15.38.

(6-Methyl-2-thioxo-2-(o-tolyl)-1,2,3,4-tetrahydropyrimidin-5-yl) (piperidin-1-yl)methanone (DHPM-KN8)

Appearance: pale brownish; IR (KBR) v/cm 3340, 3160, 2931, 1675, 1545, 1260, 1189, 1057, 765; 1 H NMR (400 MHz, DMSO-d6) δ=9.61 (—N—H, s, 1H), 8.79 (—N—H, s, 1H), 6.99 ($C_6H_2$, 2H), 6.91 ($C_6H_2$, 2H), 5.11 (—CH, 1H), 2.28 (—$CH_2$, s, 4H), 2.02 (—$CH_3$, s, 3H), 1.45 (—$CH_3$, s, 3H); 0.83 (—$CH_2$, m, 6H); $^{13}$C NMR (100 MHz, DMSO-d6) δ=173.62, 165.79, 137.72, 134.17, 130.35, 128.11, 127.81, 127.67, 126.75, 125.52, 105.79, 62.06, 53.35, 25.51, 23.72, 18.57, 15.21.

(4-(4-Chlorophenyl)-6-methyl-2-thioxo-1,2,3,4-tetrahydropyrimidin-5-yl)(piperidin-1-yl) methanone (DHPM-KN9)

Appearance: light red; IR (KBR) v/cm 3401, 3260, 2930, 1710, 1540, 1265, 1180, 1050, 735; 1 H NMR (400 MHz, DMSO-d6) δ=9.51 (—N—H, s, 1H), 8.75 (—N—H, s, 1H), 7.04 ($C_6H_2$, 2H), 6.80 ($C_6H_2$, 2H), 4.68 (—CH, 1H), 2.61 (—$CH_2$, s, 2H), 2.13 (—$CH_3$, s, 3H), 1.19 (—$CH_2$, s, 1H); 1.30 (—$CH_3$, s, 3H); 1.01 (—$CH_2$, s, 2H), 0.66 (—$CH_2$, s, 2H); $^{13}$C NMR (100 MHz, DMSO-d6) δ=174.51, 166.51, 142.41, 138.91, 133.16, 129.38, 128.94, 126.20, 106.20, 106.27, 62.89, 26.06, 24.41, 21.48, 16.09.

(6-Methyl-2-thioxo-4-(4-(trifluoromethyl)phenyl)-1,2,3,4-tetrahydropyrimidin-5-yl)(piperidin-1-yl)methanone (DHPM-KN10)

Appearance: orange; IR (KBR) v/cm 3310, 3265, 2931, 1715, 1640, 1260, 1189, 1008, 654; 1 H NMR (400 MHz, DMSO-d6) δ=9.32 (—N—H, s, 1H), 8.56 (—N—H, s, 2H), 7.08-6.47 ($C_6H_4$, 4H), 4.49 (—CH, 1H), 3.10 (—$CH_2$, m, 4H), 1.83 (—$CH_3$, s, 3H), 1.62 (—$CH_2$, s, 4H); 1.03 (—$CH_2$, s, 2H); $^{13}$C NMR (100 MHz, DMSO-d6) δ=174.15, 165.61, 160.50, 145.25, 138.01, 128.21, 127.25, 125.53, 105.27, 62.08, 43.82, 25.51, 20.83, 15.46.

(4-(4-Hydroxyphenyl)-6-methyl-2-thioxo-1,2,3,4-tetrahydropyrimidin-5-yl)(piperidin-1-yl)methanone (DHPM-KN11)

Appearance: brown; IR (KBR) v/cm 3401, 3260, 2928, 1706, 1560, 1198, 1056, 689; 1 H NMR (400 MHz, DMSO-d6) δ=9.66 (—N—H, s, 1H), 8.92 (—N—H, s, 1H), 6.82 ($C_6H_2$, d, 2H), 6.62 ($C_6H_2$, d, 2H), 4.79 (—CH, 1H), 3.66 (—OH, s, 1H), 2.39 (—$CH_2$, s, 4H), 1.55 (—$CH_3$, s, 3H); 0.93 (—$CH_2$, s, 6H); $^{13}$C NMR (100 MHz, DMSO-d6) δ=173.09, 165.64, 156.65, 133.15, 127.68, 127.18, 125.11, 114.87, 106.16, 61.65, 56.08, 25.10, 23.42, 14.93.

(4-(2-Hydroxyphenyl)-6-methyl-2-thioxo-1,2,3,4-tetrahydropyrimidin-5-yl)(piperidin-1-yl)methanone (DHPM-KN12)

Appearance: pale yellow; IR (KBR) v/cm 3368, 3265, 2920, 1689, 1515, 1218, 1125, 1055, 678; 1 H NMR (400 MHz, DMSO-d6) δ=9.63 (—N—H, s, 1H), 9.48 (—N—H, s, 1H), 8.78 (—OH, s, 1H), 7.37-6.67 ($C_6H_4$, 4H), 5.16 (—CH, 1H), 3.67 (—$CH_2$, m, 4H), 2.19 (—$CH_3$, s, 3H), 1.61 (—$CH_2$, s, 6H); $^{13}$C NMR (100 MHz, DMSO-d6) δ=176.67, 165.30, 151.05, 128.32, 125.74, 124.58, 120.84, 116.78, 62.27, 48.48, 44.01, 25.73, 22.45, 15.37.

(4-(3,4-Dihydroxyphenyl)-6-methyl-2-thioxo-1,2,3,4-tetrahydropyrimidin-5-yl)(piperidin-1-yl)methanone (DHPM-KN13)

Appearance: pale yellow; IR (KBR) v/cm 3376, 3250, 2975, 1680, 1563, 1245, 1150, 1060, 708; 1 H NMR (400 MHz, DMSO-d6) δ=9.71 (—N—H, s, 1H), 8.82 (—N—H, s, 1H), 8.98 (—OH, s, 1H), 8.97 (—OH, s, 1H) 6.61-6.35 ($C_6H_3$, 3H), 4.80 (—CH, 1H), 2.46 (—$CH_2$, s, 4H), 1.62 (—$CH_3$, s, 3H), 0.99 (—$CH_2$, s, 6H); $^{13}$C NMR (100 MHz, DMSO-d6) δ=173.63, 166.34, 145.69, 145.25, 134.33, 117.31, 115.59, 113.88, 106.88, 62.27, 56.88, 25.73, 24.08, 15.56.

(6-Methyl-4-phenyl-2-thioxo-1,2,3,4-tetrahydropyrimidin-5-yl)(pyrrolidin-1-yl)methanone (DHPM-KN14)

Appearance: pale yellow; IR (KBR) v/cm 3358, 3257, 2970, 1688, 1566, 1260, 1148, 1068, 750; 1 H NMR (400 MHz, DMSO-d6) δ=9.48 (—N—H, s, 1H), 8.88 (—N—H, s, 1H), 7.37, 7.03 ($C_6H_4$, 4H), 5.16 (—CH, 1H), 3.67 (—$CH_2$, s, 4H), 2.19 (—$CH_3$, s, 3H), 1.61 (—$CH_2$, s, 4H); $^{13}$C NMR (100 MHz, DMSO-d6) δ=176.67, 174.58, 165.30, 137.90, 129.07, 128.32, 125.74, 124.58, 116.78, 62.27, 48.48, 44.01, 25.73, 15.37.

Example 2

Anti-Tubercular Activity

The anti-tubercular activity of the designed compounds DHPM-KN 1-14, were evaluated against two types of MTB strains, namely $H_{37}Rv$ and well characterized MDR and XDR strains using the colorimetric Resazurin Microplate Assay (REMA) method. 100 mL of Middelbrook $7H_9$ broth was aseptically prepared and dispensed in each of the wells of a 96 well flat-bottomed microtiter plate with lids (Lasec, South Africa). Each of the test compounds was accurately weighed, dissolved in the appropriate solvent, and filter sterilized using a 0.2 micron polycarbonate filter. Stock solutions of the test samples were aliquoted into cryovials and stored at −20° C. A 100 mL of the test samples were added to each of the wells containing Middlebrook 7H9 broth supplemented with 0.1% Casitone, 0.5% glycerol, and 10% OADC (oleic acid, albumin, dextrose, and catalase). The test samples were then serially diluted two folds directly in the broth of the microtiter plate to the desired concentration ranging from 40-0.625 mg/mL. Inoculums from clinical isolates were prepared fresh from Middlebrook 7H11 agar plates by scraping and re-suspending loopful of colonies into Middlebrook 7H9 broth containing glass beads. The inoculum turbidity was adjusted to a McFarland number 1 standard and further diluted to 1:10 in M7H9 broth prior to the addition of 100 mL to each of the test samples and drug-free wells. Growth control and a sterile control were also included for each isolate. Sterile M7H9 broth was added to all perimeter walls to avoid evaporation during the incubation. The plate was covered, sealed in a plastic bag, and incubated at 37° C. After 8 days of incubation, 30 mL of 0.02% working solution of resazurin salt was inoculated into each microtiter well. The plates were then incubated overnight and read the following day. A positive reaction resulted in a color change from blue to pink owing to the reduction of resazurin to rezarufin which confirmed MTB cell viability/growth and, hence, drug resistance. The MICs were defined as the minimum drug concentration to inhibit the growth of the organism with no color changes present in the well. (Venugopala K. N., Sandeep C., Deb P. K., Christophe T., Pillay M., Chopra D., et al., Anti-tubercular activity and molecular docking studies of indolizine derivatives targeting mycobacterial InhA enzyme. J Enz Inhib Med Chem. 36(1); 1472-87: 2021).

The observed anti-tubercular activity of the present (6-methyl-4-substitutedphenyl-2-thioxo-1,2,3,4-tetrahydropyrimidin-5-yl)(piperidin-1-yl)methanones (DHPM-KN1-14) derivatives against H37Rv and multidrug-resistant (MDR) strains of *Mycobacterium tuberculosis* are summarized below in Table 2.

TABLE 2

| Serial No. | Compound code | Anti-tubercular activity against *Mycobacterium tuberculosis* (μg/mL) | |
| --- | --- | --- | --- |
| | | H37Rv[1] | MDR[2] |
| 1. | DHPM-KN1 | 16 | 64 |
| 2. | DHPM-KN4 | 16 | 64 |
| 3. | DHPM-KN5 | 8 | 32 |
| 4. | DHPM-KN6 | >64 | 128 |
| 5. | DHPM-KN7 | >64 | 256 |
| 6. | DHPM-KN8 | 128 | 256 |
| 7. | DHPM-KN10 | 128 | 256 |

[1]ATCC: 25177

[2]Multi-drug resistant TB (MDR-TB) - drug resistance at least to isoniazid and rifampicin It is to be understood that the present compounds, compositions, and methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

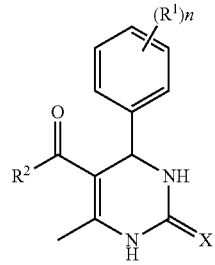

or a pharmaceutically acceptable salt, ester, stereoisomer, or solvate thereof, wherein:
   $R_1$ is trifluoromethyl;
   $R_2$ is selected from the group consisting of piperidine and pyrrolidine;
   X is S; and
   n is 1 or 2.

2. A pharmaceutical composition comprising the compound of claim 1 and a pharmaceutically acceptable carrier.

3. A compound selected from the group consisting of:
   (6-Methyl-2-thioxo-4-(4-(trifluoromethyl)phenyl)-1,2,3,4-tetrahydropyrimidin-5-yl)(piperidin-1-yl)methanone (DHPM-KN10);
   (6-Methyl-4-phenyl-2-thioxo-1,2,3,4-tetrahydropyrimidin-5-yl)(pyrrolidin-1-yl)methanone (DHPM-KN14);
   and a pharmaceutically acceptable salt, ester, stereoisomer, or solvate thereof.

* * * * *